United States Patent [19]
Dillner

[11] Patent Number: 5,989,548
[45] Date of Patent: Nov. 23, 1999

[54] PEPTIDE-BASED COMPOSITION AGAINST PAPILLOMAVIRUS INFECTION

[75] Inventor: Joakim Dillner, Danderyd, Sweden

[73] Assignee: Euro-Diagnostica AB, Malmo, Sweden

[21] Appl. No.: 08/945,168

[22] PCT Filed: Apr. 23, 1996

[86] PCT No.: PCT/SE96/00533

§ 371 Date: Dec. 18, 1997

§ 102(e) Date: Dec. 18, 1997

[87] PCT Pub. No.: WO96/33737

PCT Pub. Date: Oct. 31, 1996

[30] Foreign Application Priority Data

Apr. 24, 1995 [SE] Sweden .................................. 9501512

[51] Int. Cl.$^6$ .............................. A61K 39/00; C07K 1/00; C07H 21/04
[52] U.S. Cl. ..................................... 424/184.1; 424/185.1; 530/300; 530/403; 536/23.72; 930/220; 935/88
[58] Field of Search ............................. 424/184.1, 185.1; 530/300, 403; 536/23.72; 930/220; 935/88

[56] References Cited

FOREIGN PATENT DOCUMENTS

| 0451550 A2 | 10/1991 | European Pat. Off. . |
| WO 90/04790 | 5/1990 | WIPO . |
| WO 9118294 A1 | 11/1991 | WIPO . |
| WO 9302184 A1 | 2/1993 | WIPO . |
| WO 9501374 A1 | 1/1995 | WIPO . |

OTHER PUBLICATIONS

Immunology, Harper & Row, 1980, pp.291–295, 1980.

Journal of General Virology, vol. 71, 1990, George Strang, et al., "Human T cell responses to human papillomavirus type 16 L1 and E6 synthetic peptides: identification of T cell determinants, HLA–DR restrict ion and virus type specificity", pp. 423–431.

Journal of General Virology, vol. 189, 1992, Jian Zhou, et al. "Definition of linear antigenic regions of HPV 16 L1 capsid protein using synthetic virion–like particles", pp. 592–599.

Int. J. Cancer, vol. 45, 1990, Joakim Dillner, et al., "Mapping of linear epitopes of human papillomavirus type 16: the L1 and L2 open reading frames", pp. 529–535.

The Cancer Journal, vol. 5, No. 4, Jul. 1992, J. Dillner, "Immunobiology of papillomavirus. Prospects for vaccination" pp. 182–187.

Proc. Natl. Acad. Sci., vol. 89, Sep. 1992, Hans J. Strauss, et al., "Induction of cytotoxic T lymphocytes with peptides in vitro: Identification of candidate T–cell epitopes in human papilloma virus" pp. 7871–7875.

Archives Virology, vol. 140, 1995 J. E. Ramesar, et al., "Sequence variation in the L1 gene of human papillomavirus type 16 from Africa", pp. 1863–1870.

Journal of General Virology, vol. 75, 1994, Peter Pushko, et al., "Sequence variation in the capsid protein genes of human papillomavirus type 16" pp. 911–916.

Journal of General Virology, vol. 71, 1990, M. Mueller, et al., "Identification of seroreactive regions of the human papillomavirus type 16 proteins E4, E6, E7 and L1" pp. 2709–2717.

Journal of Medical Virology, vol. 45, 1995, P. Le Cann, et al., "Detection of Antibodies to L1, L2, and E4 Proteins of Human Papillomavirus Types 6, 11, and 16 by ELISA Using Synthetic Peptides" pp. 410–414.

Gynecologic Oncology, vol. 55, 1994, J. F. Hines, et al., "Role of Conformational Epitopes Expressed by Human Papillomavirus Major Capsid Proteins in the Serologic Detection of Infection and Prophylactic Vaccination", pp. 13–20.

Vaccine, vol. 11, No. 6, 1993, J. Cason, et al., "Towards vaccines against human papillomavirus type–16 genital infections", pp. 603–607.

*Primary Examiner*—Chris Eisenschenk
*Assistant Examiner*—Ali R. Salimi
*Attorney, Agent, or Firm*—Oblon, Spivak, McClelland, Maier & Neustadt, P.C.

[57] ABSTRACT

Pharmaceutical compositions comprising an antigenic amount of peptides derived from the L1 and L2 OFR's of human papillomavirus type 16 coupled to a carrier or in multimer form.

8 Claims, 3 Drawing Sheets

5,989,548

PEPTIDE-BASED COMPOSITION AGAINST PAPILLOMAVIRUS INFECTION

This application is a 371 of PCT/SE96/00533, filed Apr. 23, 1996.

The present invention relates to a peptide-based vaccine against papillomavirus infection.

BACKGROUND

The human papillomaviruses (HPVs) cause a variety of proliferative epithelial lesions, from common warts to pre-malignant intraepithelial neoplasias of the anogenital region (zur Hausen, 1991). Thus far, 68 different types of human papillomavirus (HPV) have been isolated (de Villiers, 1992). HPV type 16 is the predominant type found in human anogenital cancers and highgrade intraepithelial neoplasias (Lorinoz et al., 1992). The HPV capsid contains two proteins encoded by the L1 and L2 open reading frames (ORFs). The major protein of the PV capsid is an approximately 57 kDa protein encoded by L1 (Li et al., 1987); Pliacinski et al., 1984; Tomita et al., 1987). The L2 ORF codes for a 76 kDa protein which is the minor structural protein of the PV capsid (Komly et al., 1986). The HPV virion consists of an icosahedral capsid with 72 capsomeres composed of pentamers of the major capsid protein L1 (Baker et al., 1991). The function and structural location of the minor capsid protein L2 is unclear.

Neutralizing monoclonal antibodies against cottontail rabbit papillomavirus (CRPV) (Christensen & Kreider, 1991), bovine papillomavirus (BPV) (Christensen & Kreider, 1993) and HPV11 (Christensen et al., 1990) have hitherto only been generated against conformation-dependent epitopes on intact virions and it has not been possible to map their location due to the conformational dependence of these epitopes.

Immunization with an L2 protein of CRPV induces low-titered neutralizing antibodies, indicating that at least part of L2 is exposed on the virion surface (Christensen et al., 1991).

However, no specific sequences have been identified which are exposed on the virion surface of HPV. It was hypothesized that intact virions may contain surface exposed linear epitopes which could be identified by antibodies generated by immunization with peptides. A knowledge of the specific amino acid sequences of antigenic sites—exposed on intact virus particles and present in neutralizing epitopes—should enable design of effective immunogenes for vaccination.

It is well recognized that the structure of neutralizing epitopes with the ability of conferring protection is an essential requirement for the design of effective vaccines. Extensive attempts have been made to identify such neutralizing epitopes, however, without success. The problems are: 1) Immunization with an intact capsid containing conformationally sensitive epitopes may induce mostly antibodies to conformational epitopes which cannot be mapped for practical reasons. 2) Immunization with a denatured whole capsid protein will not induce antibodies against conformationally sensitive epitopes, but antibodies are preferentially made against immunodominant epitopes which are found at the inside of the capsid and these epitopes are thus not useful for vaccination.

Since it has not been possible to experimentally define the surface-exposed neutralizing epitopes, previous attempts to identify surface-exposed epitopes had to rely on computer algorithms that may identify evolutionarily variable or hydrophilic amino acid stretches which might conceivably be surface-exposed. Such algorithms have been unreliable, since they have either not worked or have only had a limited success.

DESCRIPTION OF THE INVENTION

In the experimental work, on which the present invention is based, antisera against 77 overlapping synthetic peptides from the L1 and L2 proteins of HPV16 were used to generate antipeptide antisera in guinea pigs. The resulting hyperimmune sera were tested for reactivity with intact HPV16 particles in order to identify surface-exposed epitopes. Finally, antisera against synthetic peptides from the corresponding surface-exposed sites of rabbit papillomavirus were tested for their ability to neutralize infectious rabbit papillomavirus.

A hypothesis that was made was the proposal that it should be possible to bypass the problems caused by immunodominant epitopes (either of conformational nature or located at the inside of the virus) by empiric and systematic testing of synthetic peptide immunogens for their ability to induce antibodies which are reactive with the intact virus and, in a second step, test the ability of such antibodies to neutralize infectious virus.

Some of the peptides used in the present invention have previously been described to be antigenic (WO 90/04790 and WO 91/18294), but the possibility that their antigenicity could be exploited to experimentally define surface-exposed neutralizing epitopes useful for protection against papillomavirus infection was not indicated. Nor was it suggested that a systematic synthesis and testing of analogs would result in identification of peptides with considerably improved immunogenicity. As detailed below, the exact amino acid sequence was found to be critical for the immunogenic properties of the peptides.

Thus, the present invention is directed to a vaccine against papillomavirus infection, which comprises as an immunizing component at least one peptide selected from the following groups of peptides a) to e)

```
a) (SEQ ID NO: 1) Ala Thr Val Tyr Leu Pro Pro Val Pro Val Ser Lys Val Val Ser
                                    5               10              15
``` wherein
Ala in position 1 may be substituted for Asn, Gly, Ser, or Thr,
Thr in position 2 may be substituted for Lys, Leu, Met or Gln,
Val in position 3 may be substitutde for Leu or Phe,
Leu in position 5 may be substituted for Val,
Val in position 8 may be substituted for Thr, Pro, Gln, Ala, or for the two amino-acid residues Pro Ala or Pro Asn, Pro in position 9 may be substituted for Ser,
Ser in position 11 may be substituted for Ala or Thr,
Lys in position 12 may be substituted for Arg or Thr,
Val in position 13 may be substituted for Ile, Leu or omitted,
Val in position 14 may be substituted for Ile, Leu or Pro,
Ser in position 15 may be substituted for Asn, Ala, Pro or Thr, Thr in position 4 may be substituted for Ala, Met, Val, Asp, Lys, Ser, Gly, Asn or Glu,
Val in position 5 may be substituted for Met, Leu, Ile, Ala or Thr,
Glu in position 7 may be substituted for Asp, b) (SEQ ID NO: 2) Gln Pro Leu Gly Val Gly Ile Ser Gly His Pro Leu Leu Asn Lys Leu Asp Asp Thr Glu
                                       5                  10                 15                 20 wherein
Val in position 5 may be substituted for Leu, Ile or Ala,
Ile in position 7 may be substituted for any other amino-acid residue,
His in position 10 may be substituted for Asn,
Leu in position 12 may be substituted for Tyr or Phe,
Lys in position 15 may be substituted for Arg,
Leu in position 16 may be substituted for Gln, Tyr, Asp or Phe,
Asp in position 17 may be substituted for Glu or Asn,
Thr in position 19 may be substituted for Val, Asn in position 8 may be substituted for Pro, Thr, Ala, Lys, Asp, Gln, Glu or Ser,
Val in position 9 may be substituted for Ile or Leu,
Asp in position 11 may be substituted for Asn, Glu, Thr, Ser, Ala, Gln or Gly,
Asp in position 12 may be substituted for Glu, Ala, Thr, Ser or Gln,
Leu in position 13 may be substituted for Met, Phe or Tyr, c) (SEQ ID NO: 3) Lys Gly Ser Pro Cys Thr Asn Val Ala Val Asn Pro Gly Asp Cys Pro Pro Leu Glu Leu
                                       5                  10                 15                 20 wherein
Lys, Gly and Ser in positions 1, 2 and 3, respectively, may be individually omitted, Tyr in position 14 may be substituted for Ile, Leu, Val or Met,
Ile in position 15 may be substituted for Thr, Leu, Ile, Val, Trp or Phe, and e) (SEQ ID NO: 5) Ser Thr Ile Leu Glu Asp Trp Asn Phe Gly Leu Gln Pro Pro Pro Gly Gly Thr Leu Glu
                                       5                  10                 15                 20

Pro in position 4 may be substituted for Leu, Ala, Val, Thr, Ile, Ser or Gln,
Cys in position 5 may be substituted for Ser,
Thr in position 6 may be substituted for Lys, Arg, Ala, Asn, Ser, or Gly,
Asn in position 7 may be substituted for Pro, Gln, Glu, Asn, Arg, Ser, Ala or Thr
Val in position 8 may be substituted for Asn, Asp, Pro, Thr, Ser, Ala, Arg or Gly,
Ala in position 9 may be substituted for Thr, Pro, Ser, Asn, Gln, Lys or Arg,
Val in position 10 may be substituted for Leu, Gln, Ser, Thr, Pro, Gly, Ile or omitted,
Asn in position 11 may be substituted for Ala, Ser, Gln, Thr, Arg, Pro, Val, Lys or omitted,
Pro in position 12 may be substituted for Ala, Asn, Gln, Val, Arg, Thr, Leu, Asp, Ser or omitted,
Asp in position 14 may be substituted for Glu,
Cys, Pro, Pro, Leu, Glu and Leu in positions 15, 16, 17, 18, 19 and 20, respectively, may be individually omitted, wherein
Ser in position 1 may be substituted for Pro, Asn, Lys, Ala or Thr,
Thr in position 2 may be substituted for Asp, Asn, Ser, Ala, Gln, Arg or Gly, Ile in position 3 may be substituted for Leu,
Leu in position 4 may be substituted for Ile,
Glu in position 5 may be substituted for Asp,
Asp in position 6 may be substituted for Glu, Gln, Gly or Asn,
Asn in position 8 may be substituted for Gln,
Phe in position 9 may be substituted for Val or Ile,
Gly in position 10 may be substituted for Ala, Ser or Lys,
Leu in position 11 may be substituted for Ile or Val,
Gln in position 12 may be substituted for Thr, Ala, Val, Pro, Ser or Gly,
Pro in position 13 may be substituted for Ala, Leu or Thr,
Pro in position 14 may be substituted for Ala or Val,
Pro in position 15 may be substituted for Gln, d) (SEQ ID NO: 4) Arg Ala Gly Thr Val Gly Glu Asn Val Pro Asp Asp Leu Tyr Ile
                                       5                  10                 15 wherein
Arg in position 1 may be substituted for Lys or Leu,
Ala in position 2 may be substituted for Gln, Gly, Leu or Ser,
Gly in position 3 may be substituted for Ser or Val, Gly in position 16 may be substituted for Ser, Thr, Ala or Asn,
Gly in position 17 may be substituted for Ser, Thr or Ala,
Thr in position 18 may be substituted for Ser, Glu in position 20 may be substituted for Gln or Val.

It is possible that the above listed peptides can be subject to some modifications, such as extensions, deletions and substitutions without losing their immunzing properties, and the present invention is intended to comprise such equivalent modified peptides.

In an embodiment of the invention the vaccine comprises at least two immunizing components selected from at least two different groups of peptides a) to e).

In a preferred embodiment of the invention the immunizing component(s) is (are) chosen from the peptides

```
a) Ala Thr Val Tyr Leu Pro Pro Val Pro Val Ser Lys Val Val Ser
                  5               10              15 b) Gln Pro Leu Gly Val Gly Ile Ser Gly His Pro Leu Leu Asn Lys Leu Asp Asp Thr Glu
                  5               10              15                  20 c) Lys Gly Ser Pro Cys Thr Asn Val Ala Val Asn Pro Gly Asp Cys Pro Pro Leu Glu Leu
                  5               10              15                  20 c1) Pro Ser Thr Asn Val Ala Val Asn Pro Gly Asp
                  5               10 d) Arg Ala Gly Thr Val Gly Glu Asn Val Pro Asp Asp Leu Tyr Ile
                  5               10              15 e) Ser Thr Ile Leu Glu Asp Trp Asn Phe Gly Leu Gln Pro Pro Gly Gly Thr Leu Glu
                  5               10              15                  20
```

Suitably said peptide(s) is (are) coupled to a carrier or is (are) multimer forms of the peptide(s).

Examples of carriers that may be used, and have been used, are keyhole limpet hemocyanin and tetanus toxoid. Multimer forms of the peptides may be produced by coupling the peptides to e.g. several inter-connected lysines.

As is well known in the art, the effects of a vaccine may be enhanced by the use of an adjuvant. Therefore, the vaccine according to the invention may additionally comprise an adjuvant.

Figure 1A:
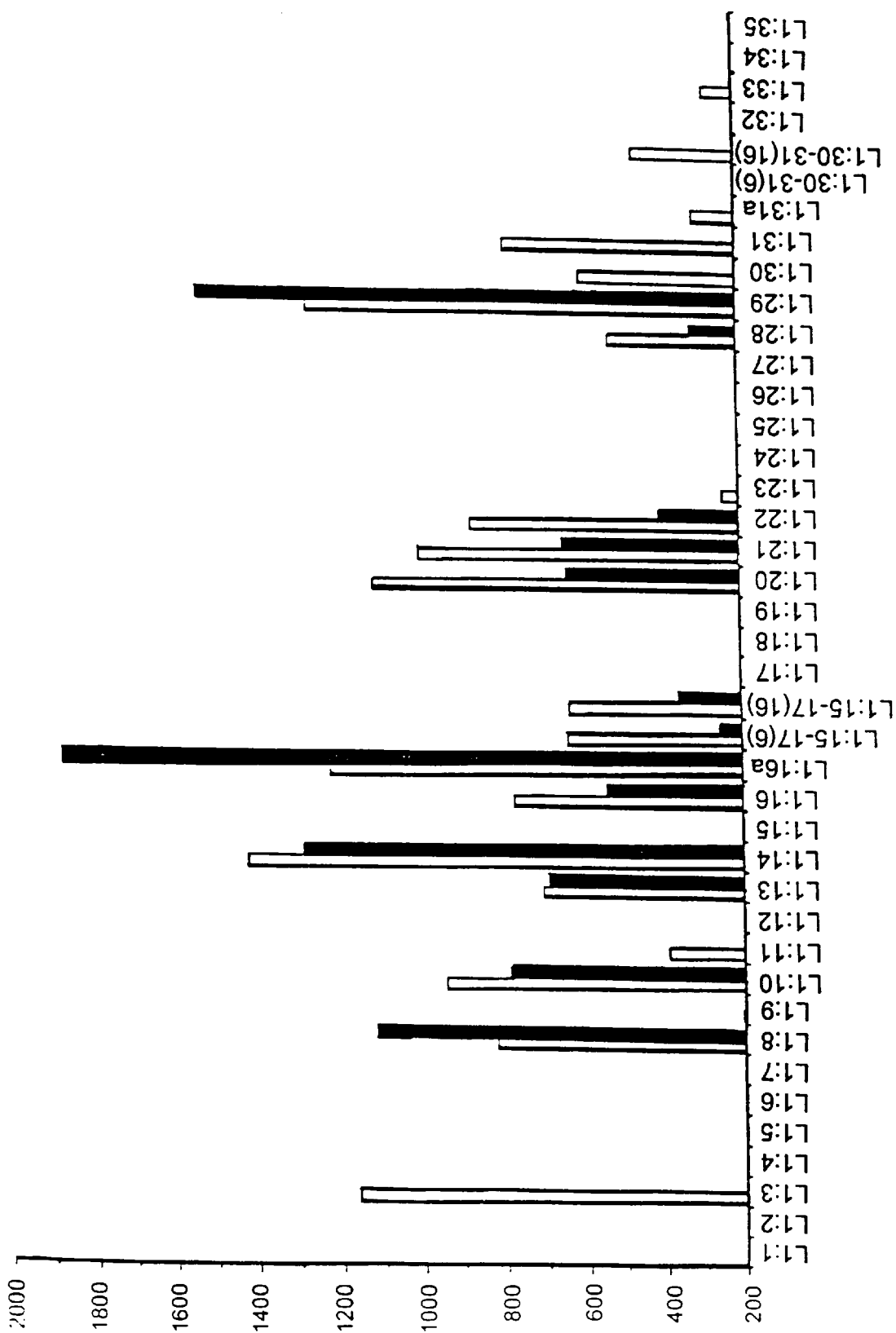
FIG. 1 shows immunoreactivity of the antipeptide antisera against (a) HPV16 L1 and (b) HPV16 L2 with intact (open bars) or disrupted (filled bars) HPV16 VLPs. Each column represents the ELISA absorbance value (OD) for one antiserum against L1 and L2 peptides reacted with the HPV16 VLPs. The number of each peptide is given below the abscissa. Peptide HPV16 L1 (L2:1) corresponds to the amino terminus of the L1 (L2) and the peptide L1:35 (L2:66) to the carboxy-terminus of the protein.

Next, the experimental work is described.

MATERIAL AND METHODS

Peptides derived from the L1 and L2 OFR:s of HPV16 were synthesized by the solid phase method as described previously (Dillner et al., 1990, and the international patent applications Nos WO 90/04790 and WO 91/18294). The peptides were conjugated to the carrier protein keyhole limpet hemocyanin and used for immunization of guinea pigs as described (Dillner et al., 1991). When tested in peptide ELISAs 56% of the immunized guinea pigs had responded with antipeptide titers of 1:10000 or more and only 5% of the immunized guinea pigs failed to respond. In experiments where the peptides were cysteine-containing they were conjugated to tetanus toxoid using the bromoacetic acid N-hydroxysuccinimide ester (Askelöf et al., 1990) whereas the other peptides were conjugated using glutaraldehyde (Dillner et al., 1991).

Capsid antigen detection. The antisera were tested by the peroxidase-antiperoxidase (PAP) staining method on formalin-fixed, paraffin-embedded sections of cervical condylomas, cervical intraepithelial neoplasia (CIN) lesions and common warts. Four $\mu$m thick sections were deparaffinized, rehydrated and treated with 3% hydrogen peroxide in PBS. After blocking with 5% milk for 60 min the sections were incubated with antipeptide antisera, diluted 1:1000. After intermediate PBS washes the sections were incubated for 1 h with anti-guinea pig immunoglobulins (Dako, Copenhagen, Denmark), diluted 1:150, for 1 h with swine anti-rabbit immunoglobulins (Dako), diluted 1:100, and for 1 h with a rabbit peroxidase-antiperoxidase complex (Dako), diluted 1:100. After a final PBS wash the antibody complex was visualized by the addition of 3-aminoethylcarbazole in acetate buffer (pH 4). Counter staining was performed with Mayer's hematoxylin for 15–30 s. The first and last section of each block were up to 1991 stained with a commercially available rabbit antiserum raised against SDS-treated BPV type 1 (Dako) and then the monospecific antiserum 16a (Dillner, et al., 1991) was used. These antisera detect PV group-specific antigens on the capsid protein and were used as a positive control.

ELISA. Guinea pig and rabbit antisera against 77 synthetic peptides derived from the L1 and L2 ORFs of HPV16 were tested for reactivity in ELISA against intact and disrupted HPV16 capsids. For disruption the capsids were diluted to 1 $\mu$g/ml in 0.1M carbonate buffer (pH 9.6) and kept at room temperature (RT) for 4 h before coating onto ELISA plates. For analysis of intact capsids the dilution was performed in phosphate buffered saline (PBS) immediately before coating. Fifty $\mu$l of the dilution was added to each well of a microtiter plate (Costar, Cambridge, Mass., USA) and the plates were incubated at +4° C. overnight. After 2 washes with ice-cold PBS the plates were blocked with 10% horse serum (heat-inactivated; Sigma, St Louis, Mo., USA) in PBS (HS-PBS) for 1 h. After discarding the blocking solution, antipeptide antisera (diluted 1:50 or 1:100 in HS-PBS) were added to the plates which were allowed to react for 2 h. After 5 washes with PBS-0.1% Tween 20 (PBS-T), peroxidase-conjugated rabbit anti-guinea pig immunoglobulins, diluted 1:2000, or goat anti-rabbit immunoglobulins, diluted 1:1000 (Dako, Copenhagen, Denmark) in HS-PBS were added to the plates which were incubated at room temperature for 2 h. After 5 washes, the plates were developed with 0.4 mg/ml of 2.2'-azino-di(3-ethylbenzthiazolinsulfonate)deammonium salt in 0.1M citrate buffer (pH 4) containing 0.9% hydrogen peroxide and the $A_{415}$-values were recorded after 15 minutes.

For two-site ("catching antibody") ELISA, the plates were coated at +4° C. overnight with the IgG fraction of rabbit antipeptide antiserum diluted 1:30 in PBS. After one wash with PBS-T and blocking with HS-PBS for 1 h the plates were incubated at 37° C. for 2 h with serial dilutions of capsids diluted either in PBS (intact particles) or in 0.1M carbonate buffer (pH 9.6) (disrupted particles). After 5 washes with PBS-T the plates were incubated for 1 h at 37° C. with guinea pig antipeptide antisera, diluted 1:100 in HS-PB. After 5 washes with PBS-T, peroxidase-conjugated guinea pig immunoglobulins, diluted 1:1000 (Dako, Copenhagen, Denmark) in 8% horse serum and 2% rabbit serum in PBS, were added to the plates which were incubated at 37° C. for 45 min. Development and recording of the color reaction were as above.

Generation of HPV16 capsids

Cloning of the capsid protein gene of a new wild-type isolate of HPV type 16.

A cervical swab sample was obtained from a healthy Swedish woman, previously determined to be infected with HPV type 16 (sample provided by Dr. Lena Dillner, Dept. of Virology, Karolinska Institute). The HPV16 L1 coding sequence was amplified by means of the polymerase chain reaction (PCR). The amplified fragment was ligated blunt end into the SmaI-digested calf intestinal alkaline phosphatase (CIAP) treated SFV expression vector, pSFV1 (kindly provided by H. Garoff and P. Liljeström, Novum, Huddinge, Sweden), a procedure which resulted in the plasmid pSFV16L1, or into EcoRV restricted CIAP treated pBluescript, a procedure which resulted in pT7-16L1. The plasmid pSFV16L1 was linearized with SpeI and capped RNA was synthesized in vitro at 37° C. for 1 h in a total volume of 50 $\mu$l of SP6 buffer (40 mM Hepes-KOH [pH 7.4], 6 mM MgOAc, 2 mM spermidine-HCl, 5 mM DTT, 1 mM $m^7(G5')ppp(5')G$, 0.5 mM GTP, 1 mM CTP, 1 mM UTP, 1 mM ATP, 50 U Rnasin and 30 U SP6 RNA polymerase. About $10^7$ baby hamster kidney cells (BHK-21) were trypsinized and washed once with PBS. Twenty to 25 $\mu$l of each recombinant RNA was used to electroporate 0.8 million cells. The cells were pulsed twice at 850 V/25 $\mu$F at room temperature. The transfected cells were resuspended in 24 ml of BHK-21 medium containing 5% fetal calf serum, 10% tryptose phosphate broth, 20 mM Hepes, 2 mM glutamine, 0.1 U/ml penicillin, 0.1 $\mu$g/ml streptomycin, and plated onto eight 35 mm cell culture plates. Cells were harvested 24 to 48 h posttransfection. For production of recombinant SFV capped RNA transcribed from pSFV15L1 or pSFV3-lacZ was electroporated into BHK-21 cells together with an equal amount of RNA produced from the helper plasmid pSFV-Helper1. Medium containing recombinant SFV (vSFV16L1 or vSFV3-lacZ) was either used for infection of BHK-21 cells directly or stored at −70° C. until used.

For infection of BHK-21 cells recombinant virus was first diluted 1:10 in minimal essential medium (MEM) containing 0.2% bovine serum albumin, 2 mM glutamine and 20 mM Hepes. A total volume of 500 $\mu$l of virus suspension was used to infect a 35 mm plate with BHK-21 cells. After 60 min, the medium containing virus was removed, 3 ml of BHK-21 medium was added to each plate and the incubation was allowed to continue for 24 to 48 h.

The cells were harvested by scraping 24 to 48 h postinfection and centrifuged at 600× g for 5 min, washed once with ice-cold PBS and stored at −70° C. Thawed cell pellets were resuspended in 10 ml of ice-cold PBS and sonicated on ice for 3×30 s. The lysates were then layered on cushions of 40% (wt/vol) sucrose-PBS and centrifuged for 2.5 h at 25,000 rpm in an W-28 rotor. The pellets were resuspended in 8 ml of PBS containing 27% (wt/wt) CsCl, transferred into quick-seal tubes and centrifuged in an SW28 rotor for 20 to 22 h at 28,000 rpm. Ten fractions were collected from each CsCl gradient and dialysed against PBS overnight. The fractions were analyzed for presence of HPV16 capsids by means of Western blotting and two-site ELISA. The fractions containing capsid proteins were also analyzed by electron microscopy and found to contain typical papillomavirus-like particles. The results are presented in FIGS. 1 and 2.

Epitopes displayed in sections of HPV-infected tissue

One hundred and fourteen cervical biopsy specimens, mostly from low-grade dysplasias and condylomas, positive for HPV6, 11, 16, 18, 31, 33 or 35 as well as 2 HPV-negative specimens were tested for expression of the HPV capsid antigen by immunostaining with an antiserum against PBV (Dako) and/or an antipeptide antiserum against an HPV group-specific epitope (Dillner, et al., 1991). Seven specimens could not be tested due to the poor quality of the sections or the very small amounts of epithelium present. Fifty two out of 107 cervical lesions (49%) were found to express the capsid antigen. For 28 out of 52 capsid antigen positive biopsies it was only possible to cut multiple consecutive sections where both the first and the last section were positive for the HPV capsid antigen. Thirty five consecutive sections from six biopsies were cut and tested with antisera to 35 peptides corresponding to the entire major capsid protein L1 (Table 1a). Five biopsies were from cervical condylomas or CIN lesions positive for HPV6, 16, 16/18, 31 or 33 and one was from a cutaneous wart. Antisera exhibiting a nuclear staining with some of the six biopsies were further tested with one additional biopsy specimen from a skin wart and six additional biopsies from cervical lesions positive for HPV 6/11, 18 or 35, 31/33/35. Stained histological sections of cervical lesions HPV-negative with our antipeptide antisera from HPV16 L1 and L2 ORF:s were used as controls. No staining was observed. Furthermore, histological sections containing HPV capsid proteins were tested with preimmune sera and no staining was detectable in the cells containing capsid antigen. Eleven of the 35 antipeptide antisera gave a specific nuclear staining in cells also positive when stained with group specific antisera for PV and in the same area of the epithelia that contained HPV-DNA when tested by ISH. Some epitopes seem to be shared by most human papillomavirus types, e.g. peptides number L1:13 and L1:16 (at the positions 182–201 and 227–246, respectively) since they were exhibited also in the HPV capsid antigens found in cutaneous warts. Most antisera only stained the genital type of HPV capsids, but one of the 11 antisera gave a type specific staining for HPV16. The number of positive cells and the intensity of the immunostainings varied with the different antipeptide sera. Strong staining intensities were mostly obtained with antisera against peptides number 13, 16, 20 and 22. The strongest staining intensities were consistently given by the antisera against the peptides 16a and 16, which were also the most cross-reactive antipeptide sera.

Thirty-one sections from two specimens, one from a HPV16 positive lesion and the other from a HPV33 positive dysplasia, were tested with 31 antisera against peptides corresponding to the entire L2 protein. Seven of the antipeptide antisera (against the peptides 38, 44, 46, 60, 61, 62 and 63;) gave a specific nuclear staining in the virusproducing tissue. Sections from 15 additional biopsies from cervical lesions infected with HPV 6, 11, 16, 18, 31, 33 and/or 35 were tested for reactivity with the seven reactive antisera. The strongest staining and the highest number of stained nuclei was obtained with antisera against the peptides L2:44, L2:46 and L2:60. The antipeptide antisera against the peptides 38, 44 and 46 stained the HPV capsid antigen of several different genital types of HPV whereas the antiserum against the peptide 60 only reacted with HPV16 and HPV33 positive lesions, and the antisera against peptides L2:61; L2:62 and L2:63 only reacted with HPV16 positive specimen(s).

Epitopes exposed on intact or disrupted HPV16 capsids

Figure 1B:
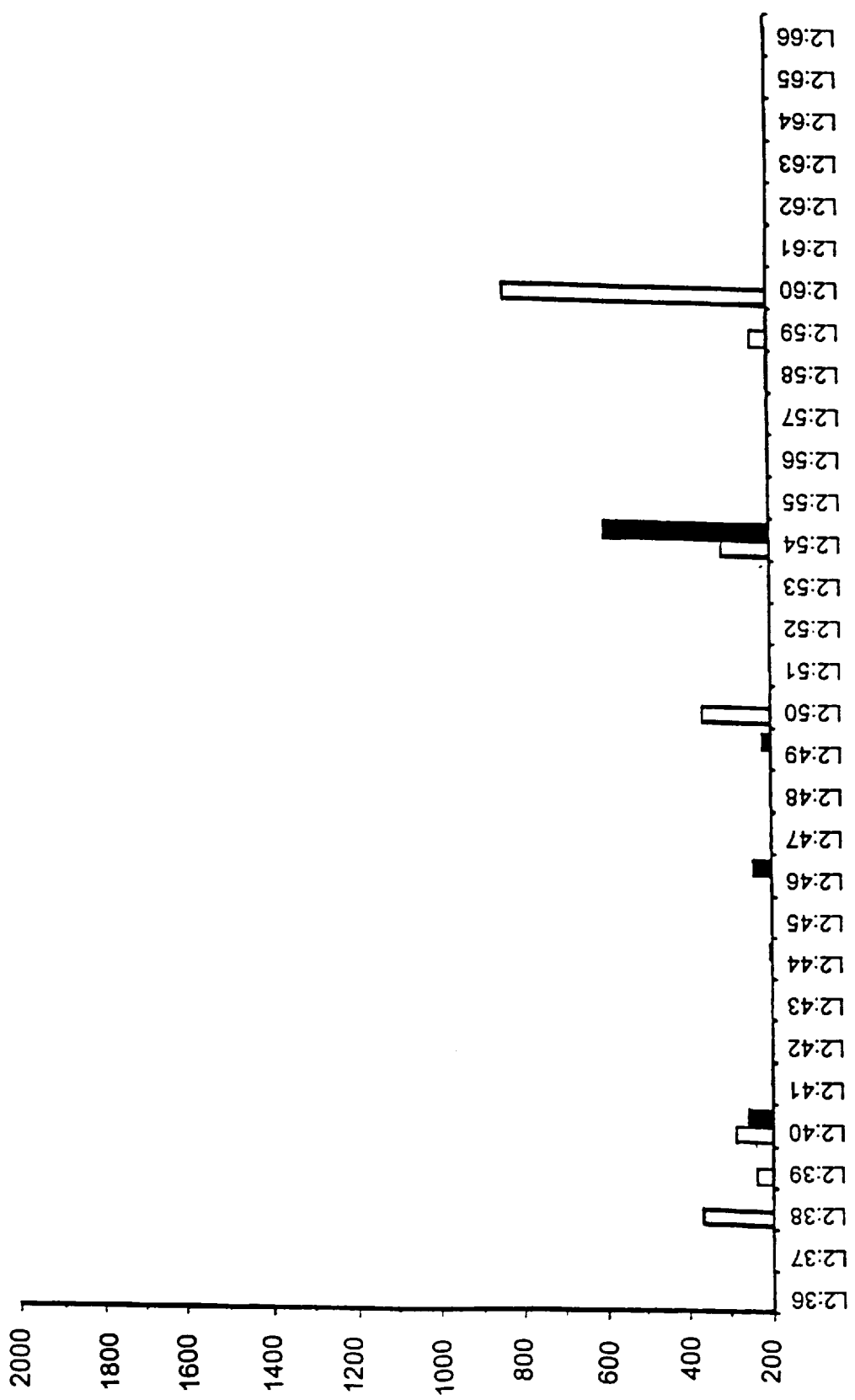

All antipeptide antibodies were screened in ELISA for reactivity with intact and disrupted HPV16 and BPV capsids as well as native and denatured HPV11 particles at a dilution of 1:100. Antisera against 19 peptides from HPV16 L1 reacted with intact HPV16 capsids (FIG. 1a). Most of the reactive sera had also been reactive with the PV capsid antigen in immunohistocytochemical stainings. Antisera against 12 peptides were also reactive with disrupted virus (FIG. 1a). Some sera, e.g. against the peptides 8, 10, 14, 16 and 29, reacted roughly as well with disrupted as with intact particles (FIG. 1a). Three antipeptide antisera (number 3, 20 and 31 were much more reactive with intact than with disrupted particles (FIG. 1a). All 31 antisera against peptides corresponding to the L2 protein of HPV16 were also tested for reactivity with HPV16 capsids. Seven antipeptide antisera reacted with intact HPV16 capsids (FIG 1b). Preimmunization serum samples from the same animals tested in parallel with the postimmunization serum samples. Weak reactivity (<30% the postimmunization serum samples) was detected in the serum of one non-immunized animal whereas no other serum samples from non-immunized animals showed any detectable reactivity (ELISA OD<0.050).

The five antisera exhibiting the strongest reactivity with intact HPV16 capsids as well as a rabbit antiserum to one of these peptides were titrated in serial 3-fold dilutions for reactivity against the immunizing peptides and intact HPV16 capsids. Two guinea pig antisera and one rabbit serum were reactive at a 1:146 000 titer (Table 2). Interestingly, two guinea pig antisera had an identical titer against HPV16 capsids and against the immunizing peptide (Table 2), which indicates that these synthetic immunogens mostly or exclusively induce antibodies reactive with intact HPV16 capsids.

Verification of epitope exposure on non-disrupted virions by two-site ELISA

Figure 2:
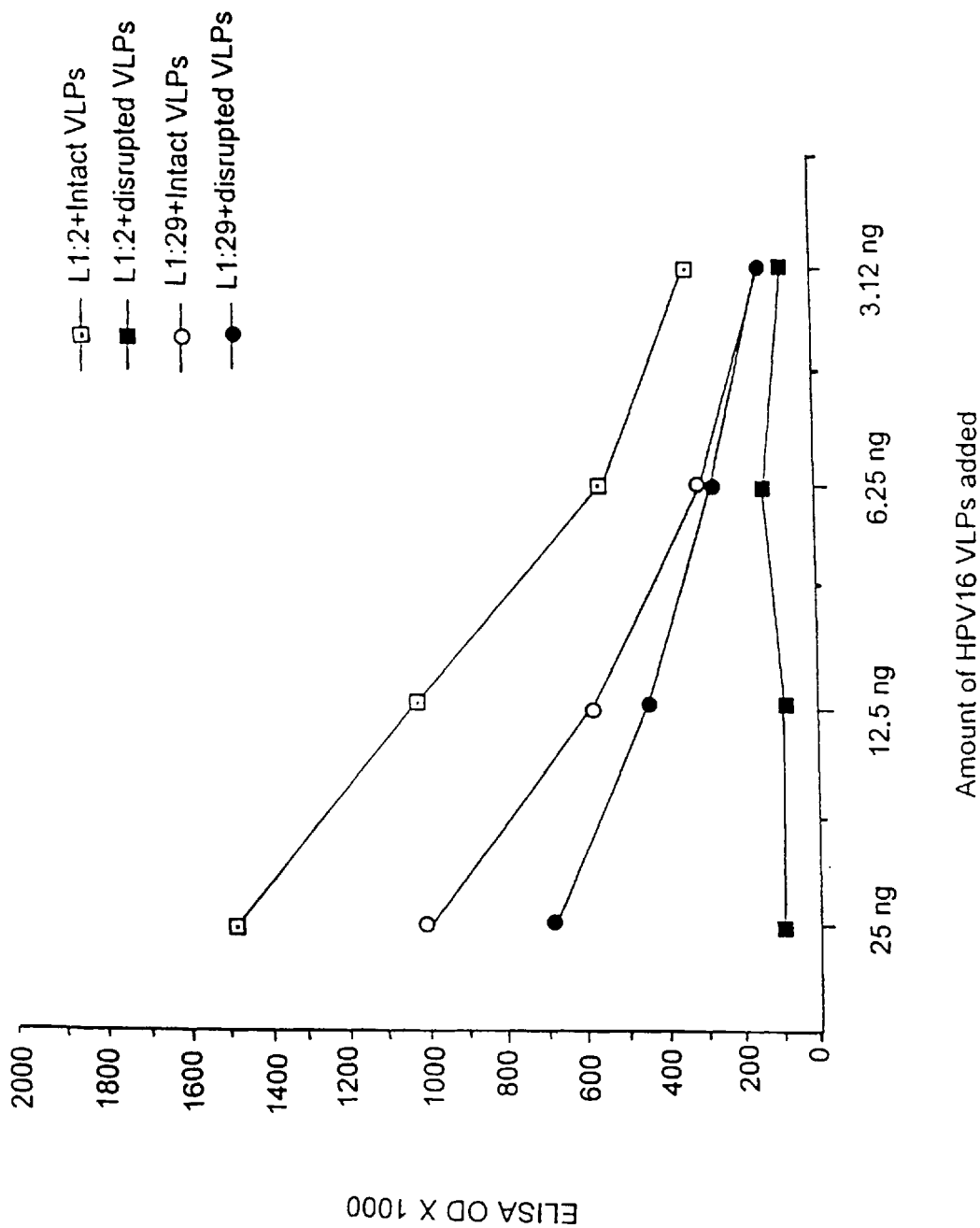
FIG. 2 shows the results obtained when intact or disrupted HPV16 capsids (VLPs) were added in serial dilutions to ELISA plates coated with antibodies against peptide L1:20 and bound virus detected with antibodies against peptide L1:20 or peptide L1:29.

Exposure to a carbonate buffer of high pH is the original method used for disrupting papillomaviruses in many classical studies. In order to quantify the disruption efficiency and exclude the possibility that the reactivity with native capsids might have been due to contaminating monomers, a catching antibody ELISA was used. ELISA plates were coated with antibodies against the peptide L1:20 and then capsids, diluted either in carbonate buffer or in PBS were added. Subsequently, antipeptide antisera against the same or other L1 peptides were allowed to react with the particles bound to the first antibody. As shown in FIG. 2, virus diluted in PBS could bind two antibodies directed against the same site, a result which demonstrates that the virus exists as multimers of the capsid protein and confirms that the L1:20 epitope indeed is exposed on intact virions. In contrast, virus diluted in carbonate buffer could only bind the L1:20 antibodies once, a result which indicates that the virus was disrupted into monomers of the capsid protein. The inability to detect bound capsids is not due to destruction of the L1:20 epitope in carbonate buffer, since it was possible to bind the capsid protein to the coated anti-L1:20 antibodies and subsequently detect it with antibodies against another antigenic site (FIG. 2).

Optimization of peptide immunogenicity

Improvement of the immunogenicity of the 4 most useful peptide immunogens was attempted by synthesizing peptide analogs and raising hyperimmune sera in guinea pigs against these peptide analogs. Tetanus toxoid (TT) was from now on used as carrier protein instead of keyhole limpet hemocyanin as TT is a carrier protein suitable for human use. The titer definition is half the maximal ELISA absorbance. The results are presented in Table 3.

For L1:3 the original peptide gave considerably better results when conjugated to TT than when conjugated to KLH. When 3 residues were removed at the C-terminal end, 3 residues at the N-terminal end and the conjugation was performed via an exogenous cysteine the same results were obtained as with the original peptide. (Compare peptides A71-23 and A71-13). However, among the various peptide modifications tried the best titers were obtained if a carbon spacer (aminobutyric acid) was added to the amino terminus (peptide A71-26).

For L1:29 addition of various spacers had very little effect, but the deletion of 2 amino terminal residues impaired the immunogenicity. Thus far, the best results have been obtained with the original peptide.

For L1:20 addition of spacers again had very little effect Addition of cysteine to the amino terminal or to the carboxy terminal ends of the peptide was performed in order to investigate if cysteine specific conjugation would represent an improvement. Omission of 2 residues in combination with a cysteine specific conjugation via a carboxy terminal cysteine residue resulted in an equally effective immunogen as the original peptide. On theoretical grounds, this peptide (A71-17) was considered the best immunogen.

For L1:14, the presence of 2 cysteine residues was considered suboptimal for cysteine-specific conjugation, and one of the cysteine residues was thus replaced by a serine residue. Both the serine replacement analogs worked well as immunogens, the one with an N-terminal serine replacement (A71-15) being somewhat better (not evident in Table 3). Three truncation analogs were made all of which had a serine replacement similar to that of A71-15. A peptide of 15-residues (A76-12) represented a considerable improvement in immunogenicity and is considered to be the best possible immunogen for this antigenic site. It is noteworthy that also a very short peptide, the peptide of 12-residues A76-14, was highly immunogenic.

Selection of peptides likely to work as immunogens for eliciting antibodies against intact virus particles also of other papillomaviruses Since the morphological structure of the papillomavirus capsid is very similar for all papillomaviruses and since there is considerable amino acid homology in the capsid protein gene of all papillomaviruses, we hypothesized that the corresponding sites would also be surface exposed and antigenic for other papillomaviruses. Several alignments for maximal homology between papillomavirus capsids proteins have been published. Selected areas of homology to the known surface-exposed sites are shown in Table 4. Accordingly, the homology in the HPV capsid protein is sufficiently strong to unambiguously perform an alignment in order to identify the maximally homologous region to the HPV16 surface exposed sites. In the case of the CRPV homologue of L1:14, the aminoterminal cysteine residue was also substituted with a serine residue and the 4 carboxy terminal residues were truncated, which resulted in a CRPV peptide that was maximally homologous with the best L1:14 analog in HPV 16 (peptide A76-12). As shown in Table 5, all four selected CRPV peptides (and also one BPV and one HPV11 peptide) induced antibodies reactive with the intact CRPV capside.

Antipeptide antibodies confer protection against papillomavirus infection

Three of the antipeptide antisera reactive with intact CRPV (number A71-2, A71-8 and A71-11) were then evaluated with respect to their ability to neutralize infectious CRPV by Dr. Francoise Breitburd. Unite des Papillomavirus, Institut Pasteur, Paris, France. The antipeptide antisera were incubated at a 1:2 dilution for 1 h at 37° C. with an infectious dose of CRPV titrated to give rise to 10–20 papillomas and then inoculated into a group of six rabbits. Pre-immunization bleeds obtained from the same animals, before peptide immunization were used as controls. Papillomas will typically appear within a few weeks post inoculation. Two antipeptide antisera (A71-2 and A71-8) were found to confer complete protection. No papillomas were seen even 3 months post inoculation. The third antiserum (A71-11) conferred partial protection. One transient papilloma was seen 3 weeks post inoculation.

Conclusions

The delineation of the antigenic structure of the HPV capsid is important for several reasons. The availability of a panel of site-directed antisera against epitopes exposed on HPV particles could be important for studies of the expression of the HPV capsid during the viral life cycle, for studies of viral infectivity and contagiousness and will enable HPV detection and typing by simple immunological techniques such as immunoperoxidase staining or two-site ELISA. Several antisera were found that showed a strong, type-restricted staining. In particular, the strongly stained L2 epitope L2:60 was found only in tissue infected by HPV16 and the closely related HPV33.

The location of the L2 protein in PV capsids is unclear (Baker, et al., 1991). We find that some antisera raised against peptides from HPV16 L2 reacted mainly with intact capsids, confirming that part of the L2 protein is exposed on the surface of the HPV capsid.

The major immunogenic linear epitopes seen by the human immune response in infected individuals has been reported previously (Dillner, et al., 1990, international patent applications Nos. WO 90/04790 and WO 91/18294). Several major immunogenic epitopes (L1:13, L1:14, L1:16 and L1:31) all correspond to major antigenic epitopes, but many of the major antigenic epitopes are poorly reactive or unreactive with human sera.

Above all, knowledge of the antigenic structure of HPV is important for the design of preventive vaccines. The present study has found several synthetic immunogens that induced high-titered responses against intact HPV16 capsids. Furthermore, several of these responses are not type-restricted to HPV16. Among the major epitopes identified L1:14 and L1:20 are promising because of the high titer obtained of the corresponding antisera against HPV16. The epitopes L1:3 and L1:29 are excellent because of their identical titers against the immunizing peptide and against the virus. The present identification and characterization of antigenic sites exposed on the HPV capsids enabled design of defined immunogens inducing protective antibodies. Thus, the peptides are useful as immunizing components in the vaccines of the present invention.

Table 1

Sequences of the 20 residue peptides overlapping by 5 residues from the HPV 16L1 (a) and L2 protein (b) that were used for immunization (SEQ ID NO: 6–72)

TABLE 1a

PEPTIDE SEQUENCES OF 20 AA OVERLAPPING PEPTIDES CORRESPONDING TO THE HPV 16L1 PROTEIN

| No. | Peptide sequence | Range |
| --- | --- | --- |
| 1 | QVTFIYILVITCYENDVNVY | (2–21) |
| 2 | DVNVYHIFFQMSLWLPSEAT | (17–36) |
| 3 | PSEATVYLPPVPVSKVVSTD | (32–51) |
| 4 | VVSTDEYVARTNIYYHAGTS | (47–66) |
| 5 | HAGTSRLLAVGHPYFPIKKP | (62–81) |
| 6 | PIKKPPNNNKILVPKVSGLQY | (77–96) |
| 7 | SGLQYRVFRIHLPDPNKFGF | (92–111) |
| 8 | NKFGFPDTSFYNPDTQRLVW | (107–126) |
| 9 | QRLVWACVGVEVGRGQPLGV | (122–141) |
| 10 | QPLGVGISGHPLLNKLDDTE | (137–156) |
| 11 | LDDTENASAYAANAGVDNRE | (152–171) |
| 12 | VDNRECISMDYKQTQLCLIG | (167–186) |
| 13 | LCLIGCKPPIGEHWGKGSPC | (182–201) |
| 14 | KGSPCTNVAVNPGDCPPLEL | (197–216) |
| 15 | PPLELINTVIQDGDMVHTGF | (212–231) |
| 16 | VHTGFGAMDFTTLQANKSEV | (227–246) |
| 17 | NKSEVPLDICTSICKYPDYI | (242–261) |
| 18 | YPDYIKMVSEPYGDSLFFYL | (257–276) |
| 19 | LFFYLRREQMFVRHLFNRAY | (272–291) |
| 20 | FNRAGTVGENVPDDLYIKGS | (287–306) |
| 21 | YIKGSGSTANLASSNYFPTP | (302–321) |
| 22 | YFPTPSGSMVTSDAQIFNKP | (317–336) |
| 23 | IFNKPYWLQRAQGHNNGICW | (332–351) |
| 24 | NGICWGNQLFVTVVDTTRST | (347–366) |
| 25 | TTRSTNMSLCAAISTSETTY | (362–381) |
| 26 | SETTYKNTNFKEYLRHGEEY | (377–396) |
| 27 | HGEEYDLQFIFQLCKITLTA | (392–411) |
| 28 | ITLTADVMTYIHSMNSTILE | (407–426) |
| 29 | STILEDWNFGLQPPPGGTLE | (422–441) |
| 30 | GGTLEDTYRFVTQAIACQKH | (437–456) |
| 31 | ACQKHTPPAPKEDDPLKKYT | (452–471) |
| 32 | LKKYTFWEVNLKEKFSADLD | (467–486) |
| 33 | SADLDQFPLGRKFLLQAGLK | (482–501) |
| 34 | QAGLKAKPKFTLGKRKATPT | (497–516) |
| 35 | KATPTTSSTSTTAKRKKRKL | (512–531) |
| 16a | VHTGFGAMDFTTLQ | (227–241) |

TABLE 1b

PEPTIDE SEQUENCES OF 20 AA OVERLAPPING PEPTIDES CORRESPONDING TO THE HPV 16 L2 PROTEIN

| No. | Peptide sequence | Range |
|---|---|---|
| 36 | RHKRSAKRTKRASATQLYKT | (2–21) |
| 37 | QLYKTCKQAGTCPPDIIPKV | (17–36) |
| 38 | IIPKVEGKTIAEQILQYGSM | (32–51) |
| 39 | QYGSMGVFFGGLGIGTGSGT | (47–66) |
| 40 | TGSGTGGRTGYIPLGTRPPT | (62–81) |
| 41 | TRPPTATDTLAPVRPPLTVD | (77–96) |
| 42 | PLTVDPVGPSDPSIVSLVEE | (92–111) |
| 43 | SLVEETSFIDAGAPTSVPSI | (107–126) |
| 44 | SVPSIPPDVSGFSITTSTDT | (122–141) |
| 45 | TSTDTTPAILDINNTVTTVT | (137–156) |
| 46 | VTTVTTHNNPTFTDPSVLQP | (152–171) |
| 47 | SVLQPPTPAETGGHFTLSSS | (167–186) |
| 48 | TLSSSTISTHNYEEIPMDTF | (182–201) |
| 49 | PMDTFIVSTNPNTVTSSTPI | (197–216) |
| 50 | SSTPIPGSRPVARLGLYSRT | (212–231) |
| 51 | LYSRTTQQVKVVDPAFVTTP | (227–246) |
| 52 | FVTTPTKLITYDNPAYEGID | (242–261) |
| 53 | YEGIDVDNTLYFSSNDNSIN | (257–276) |
| 54 | DNSINIAPDPDFLDIVALHR | (272–291) |
| 55 | VALHRPALTSRRTGIRYSRI | (287–306) |
| 56 | RYSRIGNKQTLRTRSGKSIG | (302–321) |
| 57 | GKSIGAKVHYYYDLSTIDPA | (317–336) |
| 58 | TIDPAEEIELQTITPSTYTT | (332–351) |
| 59 | STYTTTSHAASPTSINNGLY | (347–366) |
| 60 | NNGLYDIYADDFITDTSTTP | (362–381) |
| 61 | TSTTPVPSVPSTSLSGYIPA | (377–396) |
| 62 | GYIPANTTIPFGGAYNIPLV | (392–411) |
| 63 | NIPLVSGPDIPINITDQAPS | (407–426) |
| 64 | DQAPSLIPIVPGSPQYTIIA | (422–441) |
| 65 | YTIIADAGDFYLHPSYYMLRK | (437–456) |
| 66 | YMLRKRRKRLPYFFSDVSLAA | (452–471) |

Table 2

ELISA titers against immunizing peptide and intact HPV16 capsids, "VLPs" of the five antisera that had the strongest reactivity with intact HPV16 VLPs. rb=rabbit antiserum. The other antisera were made in guinea pigs. Titer definition is >2 times background reactivity.

|  | HPV16 VLPs intact | Immunizing peptide |
|---|---|---|
| L1:3 | 1:5 400 | 1:5 400 |
| L1:14 | 1:146 000 | 1:3 930 000 |
| L1:16a | 1:146 000 | 1:1 310 000 |
| L1:20 | 1:16 200 | 1:437 000 |
| L1:20, rb. | 1:146 000 | 1:1 310 000 |
| L1:29 | 1:16 200 | 1:16 200 |

Table 3

Systematic optimisation of immunogen sequence to maximize ability to elicit papillomavirus-reactive antibodies. All the peptides are derived from HPV16 and those considered to be optimal immunogens are highlighted in bold (SEQ ID NO: 73–101) X=aminobutyric acid; Z=aminohexanoic acid.

| Peptide synthesis number | Original peptide | Peptide titer | Intact virus titer | Disrupted virus titer | Sequence |
|---|---|---|---|---|---|
| A71-13 | L1:3 | 66000 | 7300 | 7300 | CATVYLPPVPVSKVVS |
| A71-23 | L1:3 | 22000 | 7300 | 7300 | PSEATVYLPPVPVSKVVSTD |
| A71-24 | L1:3 |  | 7300 | 22000 | CCCCCPSETAVYLPPVPVSKVVSTD |
| A71-25 | L1:3 | 196000 | 7300 | 7300 | GGGGPSETAVYLPPVPVSKVVSTD |
| A71-26 | L1:3 | 66000 | 66000 | 22000 | XPSEATVYLPPVPVSKVVSTD |
| A71-27 | L1:3 | 196000 | 22000 | 22000 | ZPSEATVYLPPVPVSKVVSTD |
| A71-28 | L1:29 | 66000 | 7300 | 2400 | STILEDWNFGLQPPPGGTLE |

-continued

| Peptide synthesis number | Original peptide | Peptide titer | Intact virus titer | Disrupted virus titer | Sequence |
|---|---|---|---|---|---|
| A71-30 | L1:29 | 196000 | 7300 | 2400 | GGGGSTILEDWNFGLQPPPGGTLE |
| A71-31 | L1:29 | 66000 | 2400 | 2400 | XSTILEDWNFGLQPPPGGTLE |
| A71-32 | L1:29 | 66000 | 7300 | 2400 | ZSTILEDWNFGLQPPPGGTLE |
| A71-18 | L1:29 | 2400 | 810 | 810 | CILEDWNFGLQPPPGGTLE |
| A71-33 | L1:20 | 66000 | 7300 | 7300 | FNRAGTVGENVPDDLYIKGS |
| A71-35 | L1:20 | 7300 | 270 | 800 | GGGGFNRAGTVGENVPDDLYIKGS |
| A71-36 | L1:20 | 22000 | 2400 | 7300 | XFNRAGTVGENVPDDLYIKGS |
| A71-37 | L1:20 | 7300 | 270 | 800 | ZFNRAGTVGENVPDDLYIKGS |
| A71-16 | L1:20 | 2430 | 800 | 2400 | CFNRAGTVGENVPDDLYIKGS |
| A71-17 | L1:20 | 22000 | 7300 | 7300 | FNRAGTVGENVPDDLYIC |
| A76-6 | L1:20 | 22000 | 270 | 90 | NRAGTVGENVPDDLYIXC |
| A76-7 | L1:20 | 22000 | 2400 | 800 | NRAGTVGENVPDDLYIC |
| A76-8 | L1:20 | 22000 | 2400 | 800 | RAGTVGENVPDDLYIC |
| A76-9 | L1:20 | 22000 | 800 | 270 | AGTVGENVPDDLYIC |
| A76-10 | L1:20 | 65000 | 800 | 800 | GTVGENVPDDLYIC |
| A76-11 | L1:20 | 7300 | 270 | 90 | TVGENVPDDLYIC |
| A16-14 | L1:14 | 22000 | 800 | 270 | KGSPCTNVAVNPGDCPPLEL |
| A71-14 | L1:14 | 66000 | 800 | 270 | KGSPCTNVAVNPGDSPPLEL |
| A71-15 | L1:14 | 66000 | 800 | 800 | KGSPSTNVAVNPGDCPPLEL |
| A76-12 | L1:14 | 66000 | 7300 | 7300 | KGSPSTNVAVNPGDC |
| A76-13 | L1:14 | 7300 | 7300 | 800 | SPSTNVAVNPGDCPPLEL |
| A76-14 | L1:14 | 22000 | 2700 | 2700 | PSTNVAVNPGDC |

Table 4
AMINO ACID ALIGNMENTS FOR IDENTIFYING SURFACE-EXPOSED ANTIGENIC REGIONS OF CRPV, BPV AND HPV11 BY THEIR HOMOLOGY WITH THE SURFACE-EXPOSED REGIONS OF HPV16.

The surface-exposed epitopes of HPV16 and the maximally homologous peptides of other viruses are underlined (SEQ ID NO: 102–111).

L1: REGION:

HPV16: SLWL<u>PSEATVYLPPVPVSKVV</u>STDEYVAR..

CRPV: AVWL<u>STQNKFYLPPQPVTKIPST</u>DEYVTR..

HPV11: WR<u>PSDSTVYVPPPNPVSKVVATD</u>AYVKR..

L1:14 REGION:

HPV16: GEHWG<u>KGSPCTNVAVNPGDCPPLEL</u>INTVI..

CRPV: GEHWA<u>QAKQCAEDPPQQTDCPPIEL</u>VNTVI..

L1:20 REGION:

HPV16: FVRHL<u>FNRAGTVGENVPDDLYIKGS</u>GSTAN..

CRPV: YARHF<u>FSRAGGDKENVKSRAYIKRT</u>QMQGE..

BPV: YVRHI<u>WTRGGSEKEAPTTDFYLKNN</u>KGDAT..

L1:29 REGION:

HPV16: IHSMN<u>STILEDWNFGLQPPPGGTLE</u>DTYRF..

CRPV: LHSMN<u>PTIIDNWQLSVSAQPSGTLE</u>DQYRY..

Table 5

Induction of antibodies reactive with the capsid surface of other papillomaviruses by immunization with peptides homologous to the surface-exposed epitopes on HPV16 (SEQ ID NO: 112–117).

| Peptide synthesis number | Original peptide | Derived from: | Peptide titer | Intact virus titer | Disrupted virus titer | Sequence |
| --- | --- | --- | --- | --- | --- | --- |
| A71-1 | L1:3 | HPV11 | 196000 | 2400 | 800 | PSDSTVYVPPPNPVDKVVATD |
| A71-2 | L1:3 | CRPV | 22

```
Ala Thr Val Tyr Leu Pro Pro Val Pro Val Ser Lys Val Val Ser
1               5                  10                  15
```

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Gln Pro Leu Gly Val Gly Ile Ser Gly His Pro Leu Leu Asn Lys Leu
1               5                  10                  15

Asp Asp Thr Glu
            20
```

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Lys Gly Ser Pro Cys Thr Asn Val Ala Val Asn Pro Gly Asp Cys Pro
1               5                  10                  15

Pro Leu Glu Leu
            20
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Arg Ala Gly Thr Val Gly Glu Asn Val Pro Asp Asp Leu Tyr Ile
1               5                  10                  15
```

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ser Thr Ile Leu Glu Asp Trp Asn Phe Gly Leu Gln Pro Pro Pro Gly
1               5                  10                  15

Gly Thr Leu Glu
            20
```

(2) INFORMATION FOR SEQ ID NO:6:

```
        (i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Gln Val Thr Phe Ile Tyr Ile Leu Val Ile Thr Cys Tyr Glu Asn Asp
1               5                  10                  15

Val Asn Val Tyr
           20

(2) INFORMATION FOR SEQ ID NO:7:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Asp Val Asn Val Tyr His Ile Phe Phe Gln Met Ser Leu Trp Leu Pro
1               5                  10                  15

Ser Glu Ala Thr
           20

(2) INFORMATION FOR SEQ ID NO:8:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Pro Ser Glu Ala Thr Val Tyr Leu Pro Pro Val Pro Val Ser Lys Val
1               5                  10                  15

Val Ser Thr Asp
           20

(2) INFORMATION FOR SEQ ID NO:9:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Val Val Ser Thr Asp Glu Tyr Val Ala Arg Thr Asn Ile Tyr Tyr His
1               5                  10                  15

Ala Gly Thr Ser
           20

(2) INFORMATION FOR SEQ ID NO:10:

(i) SEQUENCE CHARACTERISTICS:
            (A) LENGTH: 20 amino acids
            (B) TYPE: amino acid
            (C) STRANDEDNESS: single
```

(D) TOPOLOGY: linear (ii) MOLECULE TYPE: peptide (xi) SEQUENCE DESCRIPTION: SEQ ID NO:10:

His Ala Gly Thr Ser Arg Leu Leu Ala Val Gly His Pro Tyr Phe Pro
1               5                   10                  15

Ile Lys Lys Pro
            20

(2) INFORMATION FOR SEQ ID NO:11:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Pro Ile Lys Lys Pro Pro Asn Asn Asn Lys Ile Leu Val Pro Lys Val
1               5                   10                  15

Ser Gly Leu Gln Tyr
            20

(2) INFORMATION FOR SEQ ID NO:12:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Ser Gly Leu Gln Tyr Arg Val Phe Arg Ile His Leu Pro Asp Pro Asn
1               5                   10                  15

Lys Phe Gly Phe
            20

(2) INFORMATION FOR SEQ ID NO:13:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Asn Lys Phe Gly Phe Pro Asp Thr Ser Phe Tyr Asn Pro Asp Thr Gln
1               5                   10                  15

Arg Leu Val Trp
            20

(2) INFORMATION FOR SEQ ID NO:14:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Gln Arg Leu Val Trp Ala Cys Val Gly Val Glu Val Gly Arg Gly Gln
1               5                   10                  15

Pro Leu Gly Val
            20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Gln Pro Leu Gly Val Gly Ile Ser Gly His Pro Leu Leu Asn Lys Leu
1               5                   10                  15

Asp Asp Thr Glu
            20

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Leu Asp Asp Thr Glu Asn Ala Ser Ala Tyr Ala Ala Asn Ala Gly Val
1               5                   10                  15

Asp Asn Arg Glu
            20

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Val Asp Asn Arg Glu Cys Ile Ser Met Asp Tyr Lys Gln Thr Gln Leu
1               5                   10                  15

Cys Leu Ile Gly
            20

(2) INFORMATION FOR SEQ ID NO:18:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Leu Cys Leu Ile Gly Cys Lys Pro Pro Ile Gly Glu His Trp Gly Lys
1               5                   10                  15

```
Gly Ser Pro Cys
            20

(2) INFORMATION FOR SEQ ID NO:19:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:19:

Lys Gly Ser Pro Cys Thr Asn Val Ala Val Asn Pro Gly Asp Cys Pro
1               5                  10                  15

Pro Leu Glu Leu
            20

(2) INFORMATION FOR SEQ ID NO:20:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:20:

Pro Pro Leu Glu Leu Ile Asn Thr Val Ile Gln Asp Gly Asp Met Val
1               5                  10                  15

His Thr Gly Phe
            20

(2) INFORMATION FOR SEQ ID NO:21:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:21:

Val His Thr Gly Phe Gly Ala Met Asp Phe Thr Thr Leu Gln Ala Asn
1               5                  10                  15

Lys Ser Glu Val
            20

(2) INFORMATION FOR SEQ ID NO:22:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:22:

Asn Lys Ser Glu Val Pro Leu Asp Ile Cys Thr Ser Ile Cys Lys Tyr
1               5                  10                  15

Pro Asp Tyr Ile
            20
```

(2) INFORMATION FOR SEQ ID NO:23:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Tyr Pro Asp Tyr Ile Lys Met Val Ser Glu Pro Tyr Gly Asp Ser Leu
1               5                   10                  15

Phe Phe Tyr Leu
            20
```

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Leu Phe Phe Tyr Leu Arg Arg Glu Gln Met Phe Val Arg His Leu Phe
1               5                   10                  15

Asn Arg Ala Tyr
            20
```

(2) INFORMATION FOR SEQ ID NO:25:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Phe Asn Arg Ala Gly Thr Val Gly Glu Asn Val Pro Asp Asp Leu Tyr
1               5                   10                  15

Ile Lys Gly Ser
            20
```

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Tyr Ile Lys Gly Ser Gly Ser Thr Ala Asn Leu Ala Ser Ser Asn Tyr
1               5                   10                  15

Phe Pro Thr Pro
            20
```

(2) INFORMATION FOR SEQ ID NO:27:

(i) SEQUENCE CHARACTERISTICS:

```
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:27:

Tyr Phe Pro Thr Pro Ser Gly Ser Met Val Thr Ser Asp Ala Gln Ile
1               5                  10                  15

Phe Asn Lys Pro
            20

(2) INFORMATION FOR SEQ ID NO:28:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:28:

Ile Phe Asn Lys Pro Tyr Trp Leu Gln Arg Ala Gln Gly His Asn Asn
1               5                  10                  15

Gly Ile Cys Trp
            20

(2) INFORMATION FOR SEQ ID NO:29:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:29:

Asn Gly Ile Cys Trp Gly Asn Gln Leu Phe Val Thr Val Val Asp Thr
1               5                  10                  15

Thr Arg Ser Thr
            20

(2) INFORMATION FOR SEQ ID NO:30:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:30:

Thr Thr Arg Ser Thr Asn Met Ser Leu Cys Ala Ala Ile Ser Thr Ser
1               5                  10                  15

Glu Thr Thr Tyr
            20

(2) INFORMATION FOR SEQ ID NO:31:

(i) SEQUENCE CHARACTERISTICS:
      (A) LENGTH: 20 amino acids
      (B) TYPE: amino acid
      (C) STRANDEDNESS: single
      (D) TOPOLOGY: linear
```

(ii) MOLECULE TYPE: peptide (xi) SEQUENCE DESCRIPTION: SEQ ID NO:31:

Ser Glu Thr Thr Tyr Lys Asn Thr Asn Phe Lys Glu Tyr Leu Arg His
1               5                   10                  15

Gly Glu Glu Tyr
            20

(2) INFORMATION FOR SEQ ID NO:32:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

His Gly Glu Glu Tyr Asp Leu Gln Phe Ile Phe Gln Leu Cys Lys Ile
1               5                   10                  15

Thr Leu Thr Ala
            20

(2) INFORMATION FOR SEQ ID NO:33:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Ile Thr Leu Thr Ala Asp Val Met Thr Tyr Ile His Ser Met Asn Ser
1               5                   10                  15

Thr Ile Leu Glu
            20

(2) INFORMATION FOR SEQ ID NO:34:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Ser Thr Ile Leu Glu Asp Trp Asn Phe Gly Leu Gln Pro Pro Pro Gly
1               5                   10                  15

Gly Thr Leu Glu
            20

(2) INFORMATION FOR SEQ ID NO:35:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Gly Gly Thr Leu Glu Asp Thr Tyr Arg Phe Val Thr Gln Ala Ile Ala
1               5                   10                  15

Cys Gln Lys His
            20
```

(2) INFORMATION FOR SEQ ID NO:36:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Ala Cys Gln Lys His Thr Pro Pro Ala Pro Lys Glu Asp Asp Pro Leu
1               5                   10                  15

Lys Lys Tyr Thr
            20
```

(2) INFORMATION FOR SEQ ID NO:37:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Leu Lys Lys Tyr Thr Phe Trp Glu Val Asn Leu Lys Glu Lys Phe Ser
1               5                   10                  15

Ala Asp Leu Asp
            20
```

(2) INFORMATION FOR SEQ ID NO:38:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Ser Ala Asp Leu Asp Gln Phe Pro Leu Gly Arg Lys Phe Leu Leu Gln
1               5                   10                  15

Ala Gly Leu Lys
            20
```

(2) INFORMATION FOR SEQ ID NO:39:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Gln Ala Gly Leu Lys Ala Lys Pro Lys Phe Thr Leu Gly Lys Arg Lys
1               5                   10                  15
```

-continued

```
Ala Thr Pro Thr
            20

(2) INFORMATION FOR SEQ ID NO:40:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Lys Ala Thr Pro Thr Thr Ser Ser Thr Ser Thr Thr Ala Lys Arg Lys
1               5                   10                  15

Lys Arg Lys Leu
            20

(2) INFORMATION FOR SEQ ID NO:41:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

Val His Thr Gly Phe Gly Ala Met Asp Phe Thr Thr Leu Gln
1               5                   10

(2) INFORMATION FOR SEQ ID NO:42:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Arg His Lys Arg Ser Ala Lys Arg Thr Lys Arg Ala Ser Ala Thr Gln
1               5                   10                  15

Leu Tyr Lys Thr
            20

(2) INFORMATION FOR SEQ ID NO:43:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

Gln Leu Tyr Lys Thr Cys Lys Gln Ala Gly Thr Cys Pro Pro Asp Ile
1               5                   10                  15

Ile Pro Lys Val
            20

(2) INFORMATION FOR SEQ ID NO:44:

(i) SEQUENCE CHARACTERISTICS:
```

(A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:44:

Ile Ile Pro Lys Val Glu Gly Lys Thr Ile Ala Glu Gln Ile Leu Gln
1               5                   10                  15

Tyr Gly Ser Met
            20

(2) INFORMATION FOR SEQ ID NO:45:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:45:

Gln Tyr Gly Ser Met Gly Val Phe Phe Gly Gly Leu Gly Ile Gly Thr
1               5                   10                  15

Gly Ser Gly Thr
            20

(2) INFORMATION FOR SEQ ID NO:46:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:46:

Thr Gly Ser Gly Thr Gly Gly Arg Thr Gly Tyr Ile Pro Leu Gly Thr
1               5                   10                  15

Arg Pro Pro Thr
            20

(2) INFORMATION FOR SEQ ID NO:47:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:47:

Thr Arg Pro Pro Thr Ala Thr Asp Thr Leu Ala Pro Val Arg Pro Pro
1               5                   10                  15

Leu Thr Val Asp
            20

(2) INFORMATION FOR SEQ ID NO:48:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:48:

Pro Leu Thr Val Asp Pro Val Gly Pro Ser Asp Pro Ser Ile Val Ser
1               5                  10                  15

Leu Val Glu Glu
            20

(2) INFORMATION FOR SEQ ID NO:49:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:49:

Ser Leu Val Glu Glu Thr Ser Phe Ile Asp Ala Gly Ala Pro Thr Ser
1               5                  10                  15

Val Pro Ser Ile
            20

(2) INFORMATION FOR SEQ ID NO:50:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:50:

Ser Val Pro Ser Ile Pro Pro Asp Val Ser Gly Phe Ser Ile Thr Thr
1               5                  10                  15

Ser Thr Asp Thr
            20

(2) INFORMATION FOR SEQ ID NO:51:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:51:

Thr Ser Thr Asp Thr Thr Pro Ala Ile Leu Asp Ile Asn Asn Thr Val
1               5                  10                  15

Thr Thr Val Thr
            20

(2) INFORMATION FOR SEQ ID NO:52:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:52:

```
Val Thr Thr Val Thr Thr His Asn Asn Pro Thr Phe Thr Asp Pro Ser
1               5                   10                  15

Val Leu Gln Pro
            20
```

(2) INFORMATION FOR SEQ ID NO:53:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Ser Val Leu Gln Pro Pro Thr Pro Ala Glu Thr Gly Gly His Phe Thr
1               5                   10                  15

Leu Ser Ser Ser
            20
```

(2) INFORMATION FOR SEQ ID NO:54:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

```
Thr Leu Ser Ser Ser Thr Ile Ser Thr His Asn Tyr Glu Glu Ile Pro
1               5                   10                  15

Met Asp Thr Phe
            20
```

(2) INFORMATION FOR SEQ ID NO:55:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

```
Pro Met Asp Thr Phe Ile Val Ser Thr Asn Pro Asn Thr Val Thr Ser
1               5                   10                  15

Ser Thr Pro Ile
            20
```

(2) INFORMATION FOR SEQ ID NO:56:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

```
Ser Ser Thr Pro Ile Pro Gly Ser Arg Pro Val Ala Arg Leu Gly Leu
1               5                   10                  15
```

```
Tyr Ser Arg Thr
            20

(2) INFORMATION FOR SEQ ID NO:57:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:57:

Leu Tyr Ser Arg Thr Thr Gln Gln Val Lys Val Val Asp Pro Ala Phe
1               5                  10                  15

Val Thr Thr Pro
            20

(2) INFORMATION FOR SEQ ID NO:58:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:58:

Phe Val Thr Thr Pro Thr Lys Leu Ile Thr Tyr Asp Asn Pro Ala Tyr
1               5                  10                  15

Glu Gly Ile Asp
            20

(2) INFORMATION FOR SEQ ID NO:59:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:59:

Tyr Glu Gly Ile Asp Val Asp Asn Thr Leu Tyr Phe Ser Ser Asn Asp
1               5                  10                  15

Asn Ser Ile Asn
            20

(2) INFORMATION FOR SEQ ID NO:60:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:60:

Asp Asn Ser Ile Asn Ile Ala Pro Asp Pro Asp Phe Leu Asp Ile Val
1               5                  10                  15

Ala Leu His Arg
            20
```

(2) INFORMATION FOR SEQ ID NO:61:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

```
Val Ala Leu His Arg Pro Ala Leu Thr Ser Arg Arg Thr Gly Ile Arg
1               5                  10                  15

Tyr Ser Arg Ile
            20
```

(2) INFORMATION FOR SEQ ID NO:62:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

```
Arg Tyr Ser Arg Ile Gly Asn Lys Gln Thr Leu Arg Thr Arg Ser Gly
1               5                  10                  15

Lys Ser Ile Gly
            20
```

(2) INFORMATION FOR SEQ ID NO:63:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

```
Gly Lys Ser Ile Gly Ala Lys Val His Tyr Tyr Tyr Asp Leu Ser Thr
1               5                  10                  15

Ile Asp Pro Ala
            20
```

(2) INFORMATION FOR SEQ ID NO:64:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

```
Thr Ile Asp Pro Ala Glu Glu Ile Glu Leu Gln Thr Ile Thr Pro Ser
1               5                  10                  15

Thr Tyr Thr Thr
            20
```

(2) INFORMATION FOR SEQ ID NO:65:

(i) SEQUENCE CHARACTERISTICS:
        (A) LENGTH: 20 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:65:

Ser Thr Tyr Thr Thr Thr Ser His Ala Ala Ser Pro Thr Ser Ile Asn
1               5                   10                  15

Asn Gly Leu Tyr
            20

(2) INFORMATION FOR SEQ ID NO:66:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:66:

Asn Asn Gly Leu Tyr Asp Ile Tyr Ala Asp Asp Phe Ile Thr Asp Thr
1               5                   10                  15

Ser Thr Thr Pro
            20

(2) INFORMATION FOR SEQ ID NO:67:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:67:

Thr Ser Thr Thr Pro Val Pro Ser Val Pro Ser Thr Ser Leu Ser Gly
1               5                   10                  15

Tyr Ile Pro Ala
            20

(2) INFORMATION FOR SEQ ID NO:68:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:68:

Gly Tyr Ile Pro Ala Asn Thr Thr Ile Pro Phe Gly Gly Ala Tyr Asn
1               5                   10                  15

Ile Pro Leu Val
            20

(2) INFORMATION FOR SEQ ID NO:69:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:69:

Asn Ile Pro Leu Val Ser Gly Pro Asp Ile Pro Ile Asn Ile Thr Asp
1               5                   10                  15

Gln Ala Pro Ser
            20

(2) INFORMATION FOR SEQ ID NO:70:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

Asp Gln Ala Pro Ser Leu Ile Pro Ile Val Pro Gly Ser Pro Gln Tyr
1               5                   10                  15

Thr Ile Ile Ala
            20

(2) INFORMATION FOR SEQ ID NO:71:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

Tyr Thr Ile Ile Ala Asp Ala Gly Asp Phe Tyr Leu His Pro Ser Tyr
1               5                   10                  15

Tyr Met Leu Arg Lys
            20

(2) INFORMATION FOR SEQ ID NO:72:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:72:

Tyr Met Leu Arg Lys Arg Arg Lys Arg Leu Pro Tyr Phe Phe Ser Asp
1               5                   10                  15

Val Ser Leu Ala Ala
            20

(2) INFORMATION FOR SEQ ID NO:73:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

```
Cys Ala Thr Val Tyr Leu Pro Pro Val Pro Val Ser Lys Trp Ser
1               5                  10                  15
```

(2) INFORMATION FOR SEQ ID NO:74:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

```
Pro Ser Glu Ala Thr Val Tyr Leu Pro Pro Val Pro Val Ser Lys Val
1               5                  10                  15

Val Ser Thr Asp
        20
```

(2) INFORMATION FOR SEQ ID NO:75:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

```
Cys Cys Cys Cys Cys Pro Ser Glu Thr Ala Val Tyr Leu Pro Pro Val
1               5                  10                  15

Pro Val Ser Lys Val Val Ser Thr Asp
            20                  25
```

(2) INFORMATION FOR SEQ ID NO:76:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

```
Gly Gly Gly Gly Pro Ser Glu Thr Ala Val Tyr Leu Pro Pro Val Pro
1               5                  10                  15

Val Ser Lys Trp Ser Thr Asp
            20
```

(2) INFORMATION FOR SEQ ID NO:77:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

```
Xaa Pro Ser Glu Ala Thr Val Tyr Leu Pro Pro Val Pro Val Ser Lys
1               5                  10                  15

Val Val Ser Thr Asp
            20
```

(2) INFORMATION FOR SEQ ID NO:78:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

```
Glx Pro Ser Glu Ala Thr Val Tyr Leu Pro Pro Val Pro Val Ser Lys
1               5                  10                  15
Val Val Ser Thr Asp
            20
```

(2) INFORMATION FOR SEQ ID NO:79:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

```
Ser Thr Ile Leu Glu Asp Trp Asn Phe Gly Leu Gln Pro Pro Pro Gly
1               5                  10                  15
Gly Thr Leu Glu
            20
```

(2) INFORMATION FOR SEQ ID NO:80:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

```
Gly Gly Gly Gly Ser Thr Ile Leu Glu Asp Trp Asn Phe Gly Leu Gln
1               5                  10                  15
Pro Pro Pro Gly Gly Thr Leu Glu
            20
```

(2) INFORMATION FOR SEQ ID NO:81:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

```
Xaa Ser Thr Ile Leu Glu Asp Trp Asn Phe Gly Leu Gln Pro Pro Pro
1               5                  10                  15
Gly Gly Thr Leu Glu
            20
```

(2) INFORMATION FOR SEQ ID NO:82:

(i) SEQUENCE CHARACTERISTICS:
        (A) LENGTH: 21 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:82:

Glx Ser Thr Ile Leu Glu Asp Trp Asn Phe Gly Leu Gln Pro Pro Pro
1               5                  10                  15

Gly Gly Thr Leu Glu
            20

(2) INFORMATION FOR SEQ ID NO:83:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:83:

Cys Ile Leu Glu Asp Trp Asn Phe Gly Leu Gln Pro Pro Pro Gly Gly
1               5                  10                  15

Thr Leu Glu (2) INFORMATION FOR SEQ ID NO:84:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:84:

Phe Asn Arg Ala Gly Thr Val Gly Glu Asn Val Pro Asp Asp Leu Tyr
1               5                  10                  15

Ile Lys Gly Ser
            20

(2) INFORMATION FOR SEQ ID NO:85:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:85:

Gly Gly Gly Gly Phe Asn Arg Ala Gly Thr Val Gly Glu Asn Val Pro
1               5                  10                  15

Asp Asp Leu Tyr Ile Lys Gly Ser
            20

(2) INFORMATION FOR SEQ ID NO:86:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:86:

Xaa Phe Asn Arg Ala Gly Thr Val Gly Glu Asn Val Pro Asp Asp Leu
1               5                   10                  15

Tyr Ile Lys Gly Ser
            20

(2) INFORMATION FOR SEQ ID NO:87:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:87:

Glx Phe Asn Arg Ala Gly Thr Val Gly Glu Asn Val Pro Asp Asp Leu
1               5                   10                  15

Tyr Ile Lys Gly Ser
            20

(2) INFORMATION FOR SEQ ID NO:88:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:88:

Cys Phe Asn Arg Ala Gly Thr Val Gly Glu Asn Val Pro Asp Asp Leu
1               5                   10                  15

Tyr Ile Lys Gly Ser
            20

(2) INFORMATION FOR SEQ ID NO:89:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:89:

Phe Asn Arg Ala Gly Thr Val Gly Glu Asn Val Pro Asp Asp Leu Tyr
1               5                   10                  15

Ile Cys (2) INFORMATION FOR SEQ ID NO:90:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:90:

Asn Arg Ala Gly Thr Val Gly Glu Asn Val Pro Asp Asp Leu Tyr Ile
1               5                   10                  15

Xaa Cys (2) INFORMATION FOR SEQ ID NO:91:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:91:

Asn Arg Ala Gly Thr Val Gly Glu Asn Val Pro Asp Asp Leu Tyr Ile
1               5                   10                  15
Cys (2) INFORMATION FOR SEQ ID NO:92:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:92:

Arg Ala Gly Thr Val Gly Glu Asn Val Pro Asp Asp Leu Tyr Ile Cys
1               5                   10                  15

(2) INFORMATION FOR SEQ ID NO:93:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:93:

Ala Gly Thr Val Gly Glu Asn Val Pro Asp Asp Leu Tyr Ile Cys
1               5                   10                  15

(2) INFORMATION FOR SEQ ID NO:94:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:94:

Gly Thr Val Gly Glu Asn Val Pro Asp Asp Leu Tyr Ile Cys
1               5                   10

(2) INFORMATION FOR SEQ ID NO:95:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:95:

Thr Val Gly Glu Asn Val Pro Asp Asp Leu Tyr Ile Cys
1               5                   10

NFORMATION FOR SEQ ID NO:96:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

Lys Gly Ser Pro Cys Thr Asn Val Ala Val Asn Pro Gly Asp Cys Pro
1               5                   10                  15

Pro Leu Glu Leu
            20

(2) INFORMATION FOR SEQ ID NO:97:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

Lys Gly Ser Pro Cys Thr Asn Val Ala Val Asn Pro Gly Asp Ser Pro
1               5                   10                  15

Pro Leu Glu Leu
            20

(2) INFORMATION FOR SEQ ID NO:98:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

Lys Gly Ser Pro Ser Thr Asn Val Ala Val Asn Pro Gly Asp Cys Pro
1               5                   10                  15

Pro Leu Glu Leu
            20

(2) INFORMATION FOR SEQ ID NO:99:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:99:

Lys Gly Ser Pro Ser Thr Asn Val Ala Val Asn Pro Gly Asp Cys
1               5                   10                  15

(2) INFORMATION FOR SEQ ID NO:100:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:100:

Ser Pro Ser Thr Asn Val Ala Val Asn Pro Gly Asp Cys Pro Pro Leu
1               5                   10                  15

Glu Leu (2) INFORMATION FOR SEQ ID NO:101:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:101:

Pro Ser Thr Asn Val Ala Val Asn Pro Gly Asp Cys
1               5                   10

(2) INFORMATION FOR SEQ ID NO:102:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:102:

Ser Leu Trp Leu Pro Ser Glu Ala Thr Val Tyr Leu Pro Pro Val Pro
1               5                   10                  15

Val Ser Lys Val Val Ser Thr Asp Glu Tyr Val Ala Arg
            20                  25

(2) INFORMATION FOR SEQ ID NO:103:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

Ala Val Trp Leu Ser Thr Gln Asn Lys Phe Tyr Leu Pro Pro Gln Pro
1               5                   10                  15

Val Thr Lys Ile Pro Ser Thr Asp Glu Tyr Val Thr Arg
            20                  25

(2) INFORMATION FOR SEQ ID NO:104:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

Trp Arg Pro Ser Asp Ser Thr Val Tyr Val Pro Pro Asn Pro Val
1               5                  10                 15

Ser Lys Val Val Ala Thr Asp Ala Tyr Val Lys Arg
                20                  25

(2) INFORMATION FOR SEQ ID NO:105:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Gly Glu His Trp Gly Lys Gly Ser Pro Cys Thr Asn Val Ala Val Asn
1               5                  10                 15

Pro Gly Asp Cys Pro Pro Leu Glu Leu Ile Asn Thr Val Ile
                20                  25                 30

(2) INFORMATION FOR SEQ ID NO:106:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

Gly Glu His Trp Ala Gln Ala Lys Gln Cys Ala Glu Asp Pro Pro Gln
1               5                  10                 15

Gln Thr Asp Cys Pro Pro Ile Glu Leu Val Asn Thr Val Ile
                20                  25                 30

(2) INFORMATION FOR SEQ ID NO:107:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Phe Val Arg His Leu Phe Asn Arg Ala Gly Thr Val Gly Glu Asn Val
1               5                  10                 15

Pro Asp Asp Leu Tyr Ile Lys Gly Ser Gly Ser Thr Ala Asn
                20                  25                 30

(2) INFORMATION FOR SEQ ID NO:108:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:108:

Tyr Ala Arg His Phe Phe Ser Arg Ala Gly Gly Asp Lys Glu Asn Val

```
                1               5                    10                   15
Lys Ser Arg Ala Tyr Ile Lys Arg Thr Gln Met Gln Gly Glu
                         20                   25                   30

(2) INFORMATION FOR SEQ ID NO:109:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:109:

Tyr Val Arg His Ile Trp Thr Arg Gly Gly Ser Glu Lys Glu Ala Pro
1               5                   10                  15
Thr Thr Asp Phe Tyr Leu Lys Asn Asn Lys Gly Asp Ala Thr
                20                  25                  30

(2) INFORMATION FOR SEQ ID NO:110:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:110:

Ile His Ser Met Asn Ser Thr Ile Leu Glu Asp Trp Asn Phe Gly Leu
1               5                   10                  15
Gln Pro Pro Pro Gly Gly Thr Leu Glu Asp Thr Tyr Arg Phe
                20                  25                  30

(2) INFORMATION FOR SEQ ID NO:111:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:111:

Leu His Ser Met Asn Pro Thr Ile Ile Asp Asn Trp Gln Leu Ser Val
1               5                   10                  15
Ser Ala Gln Pro Ser Gly Thr Leu Glu Asp Gln Tyr Arg Tyr
                20                  25                  30

(2) INFORMATION FOR SEQ ID NO:112:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:112:

Pro Ser Asp Ser Thr Val Tyr Val Pro Pro Asn Pro Val Asp Lys
1               5                   10                  15
Val Val Ala Thr Asp
                20
```

(2) INFORMATION FOR SEQ ID NO:113:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:113:

Ser Thr Gln Asn Lys Phe Tyr Leu Pro Pro Gln Pro Val Thr Lys Ile
1               5                   10                  15

Pro Ser Thr Asp
            20

(2) INFORMATION FOR SEQ ID NO:114:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:114:

Phe Ser Arg Ala Gly Gly Asp Lys Glu Asn Val Lys Ser Arg Ala Tyr
1               5                   10                  15

Ile Lys Arg Thr
            20

(2) INFORMATION FOR SEQ ID NO:115:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:115:

Trp Thr Arg Gly Gly Ser Glu Lys Glu Ala Pro Thr Thr Asp Phe Tyr
1               5                   10                  15

Leu Lys Asn Asn
            20

(2) INFORMATION FOR SEQ ID NO:116:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:116:

Pro Thr Ile Ile Asp Asn Trp Gln Leu Ser Val Ser Ala Gln Pro Ser
1               5                   10                  15

Gly Thr Leu Glu
            20

(2) INFORMATION FOR SEQ ID NO:117:

```
    (i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:117:

Gln Ala Lys Gln Ser Ala Glu Asp Pro Pro Gln Gln Thr Asp Cys
1               5                   10                  15
```

I claim:
1. A pharmaceutical composition, comprising:
a pharmaceutical acceptable carrier and an antigenic amount of a peptide selected from the group consisting of peptides a) to e)
a) SEQ ID NO: 1, Ala Thr Val Tyr Leu Pro Pro Val Pro Val Ser Lys Val Val Ser 5 10 15 wherein
Ala in position 1 may be substituted for Asn, Gly, Ser, or Thr,
Thr in position 2 may be substituted for Lys, Leu, Met or Gln,
Val in position 3 may be substituted for Leu or Phe,
Leu in position 5 may be substituted for Val,
Val in position 8 may be substituted for Thr, Pro, Gln, Ala, or for the two amino-acid residues Pro Ala or Pro Asn,
Pro in position 9 may be substituted for Ser,
Ser in position 11 may be substituted for Ala or Thr,
Lys in position 12 may be substituted for Arg or Thr,
Val in position 13 may be substituted for Ile, Leu or omitted,
Val in position 14 may be substituted for Ile, Leu or Pro,
Ser in position 15 may be substituted for Asn, Ala, Pro or Thr,
b) SEQ ID NO: 2, Gln Pro Leu Gly Val Gly Ile Ser Gly His Pro Leu Leu Asn Lys Leu Asp Asp Thr Glu 5 10 15 20 wherein
Val in position 5 may be substituted for Leu, Ile or Ala,
Ile in position 7 may be substituted for any other amino-acid residue,
His in position 10 may be substituted for Asn,
Leu in position 12 may be substituted for Tyr or Phe,
Lys in position 15 may be substituted for Arg,
Leu in position 16 may be substituted for Gln, Tyr, Asp or Phe,
Asp in position 17 may be substituted for Glu or Asn,
Thr in position 19 may be substituted for Val,
c) SEQ ID NO: 3, Lys Gly Ser Pro Cys Thr Asn Val Ala Val Asn Pro Gly Asp Cys Pro Pro Leu Glu Leu 5 10 15 20 wherein
Lys, Gly and Ser in positions 1, 2 and 3, respectively, may be individually omitted,
Pro in position 4 may be substituted for Leu, Ala, Val, Thr, Ile, Ser or Gln,
Cys in position 5 may be substituted for Ser.
Thr in position 6 may be substituted for Lys, Arg, Ala, Asn, Ser, or Gly,
Asn in position 7 may be substituted for Pro, Gln, Glu, Asn, Arg, Ser, Ala or Thr Val in position 8 may be substituted for Asn, Asp, Pro, Thr, Ser, Ala, Arg or Gly,
Ala in position 9 may be substituted for Thr, Pro, Ser, Asn, Gln, Lys or Arg,
Val in position 10 may be substituted for Leu, Gln, Ser, Thr, Pro, Gly, Ile or omitted,
Asn in position 11 may be substituted for Ala, Ser, Gln, Thr, Arg, Pro, Val, Lys or omitted,
Pro in position 12 may be substituted for Ala, Asn, Gln, Val, Arg, Thr, Leu, Asp, Ser or omitted,
Asp in position 14 may be substituted for Glu,
Cys, Pro, Pro, Leu, Glu and Leu in positions 15, 16, 17, 18, 19 and 20, respectively, may be individually omitted,
d) SEQ ID NO: 4, Arg Ala Gly Thr Val Gly Glu Asn Val Pro Asp Asp Leu Tyr Ile 5 10 15 wherein
Arg in position 1 may be substituted for Lys or Leu,
Ala in position 2 may be substituted for Gln, Gly, Leu or Ser,
Gly in position 3 may be substituted for Ser or Val,
Thr in position 4 may be substituted for Ala, Met, Val, Asp, Lys, Ser, Gly, Asn or Glu,
Val in position 5 may be substituted for Met, Leu, Ile, Ala or Thr,
Glu in position 7 may be substituted for Asp,
Asn in position 8 may be substituted for Pro, Thr, Ala, Lys, Asp, Gln, Glu or Ser,
Val in position 9 may be substituted for Ile or Leu,
Asp in position 11 may be substituted for Asn, Glu, Thr, Ser, Ala, Gln or Gly,
Asp in position 12 may be substituted for Glu, Ala, Thr, Ser or Gln,
Leu in position 13 may be substituted for Met, Phe or Tyr,
Tyr in position 14 may be substituted for Ile, Leu, Val or Met,
Ile in position 15 may be substituted for Thr, Leu, Ile, Val, Trp or Phe, and
e) SEQ ID NO: 5, Ser Thr Ile Leu Glu Asp Trp Asn Phe Gly Leu Gln Pro Pro Pro Gly Gly Thr Leu Glu 5 10 15 20 wherein
Ser in position 1 may be substituted for Pro, Asn, Lys, Ala or Thr,
Thr in position 2 may be substituted for Asp, Asn, Ser, Ala, Gln, Arg or Gly,
Ile in position 3 may be substituted for Leu,
Leu in position 4 may be substituted for Ile,
Glu in position 5 may be substituted for Asp,
Asp in position 6 may be substituted for Glu, Gln, Gly or Asn, Asn in position 8 may be substituted for Gln,
Phe in position 9 may be substituted for Val or Ile,
Gly in position 10 may be substituted for Ala, Ser or Lys,
Leu in position 11 may be substituted for Ile or Val,
Gln in position 12 may be substituted for Thr, Ala, Val, Pro, Ser or Gly,
Pro in position 13 may be substituted for Ala, Leu or Thr,
Pro in position 14 may be substituted for Ala or Val,
Pro in position 15 may be substituted for Gln,
Gly in position 16 may be substituted for Ser, Thr, Ala or Asn,
Gly in position 17 may be substituted for Ser, Thr or Ala,
Thr in position 18 may be substituted for Ser,
Glu in position 20 may be substituted for Gln or Val.

2. The composition of claim 1, which comprises at least two antigenic components selected from at least two different groups of peptides a) to e).

3. The composition of claim 1 or 2, wherein said antigenic component is chosen from the peptides
   a) SEQ ID NO: 1
      Ala Thr Val Tyr Leu Pro Pro Val Pro Val Ser Lys Val Val Ser 5 10 15
   b) SEQ ID NO: 2
      Gln Pro Leu Gly Val Gly Ile Ser Gly His Pro Leu Leu Asn Lys Leu Asp Asp Thr Glu 5 10 15 20
   c) SEQ ID NO: 3
      Lys Gly Ser Pro Cys Thr Asn Val Ala Val Asn Pro Gly Asp Cys Pro Pro Leu Glu Leu 5 10 15 20
   c1) SEQ ID NO: 101
      pro Ser Thr Asn Val Asn Pro Gly Asp Cys 5 10
   d) SEQ ID NO: 4
      Arg Ala Gly Thr Val Gly Glu Asn Val Pro Asp Asp Leu Tyr Ile 5 10 15
   e) SEQ ID NO: 5
      Ser Thr Ile Leu Glu Asp Trp Asn Phe Gly Leu Gln Pro Pro Pro Gly Gly Thr Leu Glu 5 10 15 20.

4. The composition of claim 1, wherein the peptide is e).

5. The composition of claim 1, further comprising an adjuvant.

6. The composition of claim 2, further comprising an adjuvant.

7. The composition of claim 3, further comprising an adjuvant.

8. The composition of claim 4, further comprising an adjuvant.

* * * * *